(12) United States Patent
Corcoran (10) Patent No.: US 6,973,821 B2
(45) Date of Patent: Dec. 13, 2005

(54) COMPACTION QUALITY ASSURANCE BASED UPON QUANTIFYING COMPACTOR INTERACTION WITH BASE MATERIAL

(75) Inventor: Paul T. Corcoran, Washington, IL (US)

(73) Assignee: Caterpillar Inc., Peoria, IL (US)

( * ) Notice: Subject to any disclaimer, the term of this patent is extended or adjusted under 35 U.S.C. 154(b) by 0 days.

(21) Appl. No.: 10/782,299

(22) Filed: Feb. 19, 2004

(65) Prior Publication Data

US 2005/0183512 A1    Aug. 25, 2005

(51) Int. Cl.[7] .............................................. G01N 3/00
(52) U.S. Cl. ....................................................... 73/78
(58) Field of Search .............................. 73/818, 78, 84, 73/573, 594, 579; 324/637; 364/550; 440/72, 440/133.05; 250/34.8, 358.1

(56) References Cited

U.S. PATENT DOCUMENTS

| | | | |
|---|---|---|---|
| 4,979,197 A | * | 12/1990 | Troxler et al. ................ 378/90 |
| 5,493,494 A | | 2/1996 | Henderson |
| 5,942,679 A | | 8/1999 | Sandstrom |
| 5,952,561 A | | 9/1999 | Jaselskis et al. |
| 6,122,601 A | * | 9/2000 | Swanson et al. ............ 702/137 |
| 6,188,942 B1 | | 2/2001 | Corcoran et al. |
| 6,460,006 B1 | * | 10/2002 | Corcoran ..................... 702/137 |
| 6,747,949 B1 | * | 6/2004 | Futral ......................... 370/231 |

* cited by examiner

Primary Examiner—Max Noori
Assistant Examiner—T. Miller
(74) Attorney, Agent, or Firm—Liell & McNeil (57) ABSTRACT

In most construction processes, some quality assurance compaction test must be performed on a base material before further construction can take place on or relative to the compacted base material. In order to avoid costly downtime associated with waiting for a quality assurance test to be performed, the present invention contemplates generating compaction quality assurance data using on-board generated compaction quality control data. The quality control compaction data is based upon quantifying a sinkage deformation interaction between the compactor and the base material. The interaction might include monitoring an effective roller radius of the compactor, or an amount of energy transferred or consumed when the compactor moves over the base material, or even measuring a rut depth caused by the compactor. The compaction quality assurance data can be indicative of a proof rolling test result, a walk out test result, a penetrometer test result, a base material density test result, or possibly even a compactor sinkage into the base material.

20 Claims, 3 Drawing Sheets

COMPACTION QUALITY ASSURANCE BASED UPON QUANTIFYING COMPACTOR INTERACTION WITH BASE MATERIAL

TECHNICAL FIELD

This invention relates generally to assuring quality compaction of a base material, and more particularly to an on-board determination of compaction quality based upon a sinkage deformation interaction between the compactor and the base material.

BACKGROUND

Achieving soil, asphalt, waste, and other earthen material compaction requirements is critical to earthwork constructions including road beds, pavements, foundations, dams, runways, landfill liners, etc. Compaction is required most often to improve the load bearing capacity of earthen materials, improve their strength and resistance to failure, and/or improve permeability. In most instances, some secondary measurement of compaction quality is necessary in order to proceed to a next stage in construction after a base material has been compacted. In other words, the construction project must be delayed until a compaction quality assurance test is performed and passed.

In the past, many different quality assurance tests have been devised that are often dependent on what the based material is, and the preferences of the controlling authority where the base material is located. For instance, the Iowa Department of Transportation requires a proof rolling test to be performed on a base material using a truck having certain weight and speed requirements to produce ruts less than a prescribed depth when traveling over the supposedly compacted base material. If the prescribed truck at the prescribed speed produces ruts greater than the prescribed depth, then the base material compaction is deemed unsatisfactory and must be further compacted before further construction on the base material can be approved. In another jurisdiction, a nuclear density measure of the base material must be performed, and the test result must come within certain prescribed standards before further construction on the base material can proceed. In relation to soil or waste compaction, some jurisdictions may require a walk out test to confirm that the base material has achieved a prescribed level of compaction. Walk out occurs when a compactor with a tipped roller becomes supported on the base material by the roller tips such that the compactor roller surface is lifted off the base material. In still other instances and/or jurisdictions, a penetrometer test might be performed using a prescribed device in a prescribed manner.

While most of the these quality assurance techniques have proven over time to be valid means by which the compaction quality of a base material can be assured, there are drawbacks to this method of progressing through a construction project. For instance, while in most instances a base material to be compacted has a relatively large area, most, if not all, of the accepted quality assurance techniques only check a compaction status of a very small portion of the compacted area. Since the level of compaction can vary substantially over an area to be compacted, a quality assurance test at one location can be completely inaccurate with regard to another location some distance away from the tested area. Thus, in most cases only a very small fraction of an earthen structure is actually validated to meet compaction requirements. Thus, inadequate compaction in one area can, and sometimes does, go undetected after a quality assurance test at another location on the base material suggests that an entire area has been satisfactorily compacted.

Another drawback in current construction processes involves the costs of waiting for a quality assurance test to be initiated and performed after completion of the compaction process. In other words, the down time involved in waiting to proceed to a next stage of construction after completion of a compaction process can increase inefficiencies and substantially increase the overall costs of a construction project. In addition, if the quality assurance test indicates a failure to meet compaction specifications, further delays can occur in determining what, and how extensive a rework will be required to correct for the failure(s).

In recent years, there have been efforts employed to use a variety of quality control techniques to reduce occurrences of quality assurance test failures in order to reduce costs associated with having to re-compact an area in order to satisfy compaction specifications at a given site. Co-owned U.S. Pat. No. 6,188,942 to Corcoran et al. describes a method and apparatus for determining the performance of a compaction machine based on energy transfer. This patent insightfully recognizes that the dynamic energy interaction of a compactor moving over a base material can provide a basis for generating real time compaction quality control data so that the operator can monitor the compaction status of each location of the base material. While this compaction monitoring technique can improve a operator's confidence that the base material will pass a compaction quality assurance test, the technique does nothing for the costs associated with waiting for the compaction quality assurance test to occur and be completed.

In U.S. Pat. No. 5,942,679 another compaction monitoring strategy is detailed, presumably to avoid the costs associated with failing a quality assurance compaction test. In this patent, a compacting machine continuously moves behind a paver machine. Based upon the pavement material, temperatures of both the material and ambient temperatures and other sensed factors, the reference teaches that the pavement can be satisfactorily compacted with some integer number of passes by the compacting machine. The system continuously monitors the position of the compactor and graphically displays to the operator a grid map showing the number of passes that have been completed for each unit of surface area of the pavement to be compacted. While this system can be affective in monitoring the number of passes that the compactor has made over each location on a pavement surface, it provides only predictions regarding the actual compaction status of any location. Thus, this system must rely heavily on the accuracy of assumptions that go into predicting the number of necessary passes to compact pavement under a set of conditions, which themselves are likely in a state of flux.

In still another technique taught in co-owned U.S. Pat. No. 5,493,494, a three dimensional global positioning system strategy is used to continuously monitor the elevation of the compacting machine at each location on a base material to be compacted. With each pass over a given location, the system compares the current elevation of the compacting machine to the elevation in a prior pass. Based upon these comparisons, the system draws certain conclusions as to the compaction status of the underlying base material. This strategy is taught as being particularly applicable to landfill compaction operations where the base material itself may be changing with each successive pass due to the addition of uncompacted waste material between passes. Nevertheless, this system could have promise, but does suffer from the drawback of reliance upon referencing an off-board elevational reference (GPS Satellite or Elevation Bench Mark) in order to perform as described.

In other known strategies, a density measuring device may be attached to a compactor, but accurate use of the device requires that the compactor remain stationary for some substantial period of time. In still another instance, it is known to sense via accelerometers a dynamic response of the compacting machine to a vibration sent into the underlying base material, and then estimate density based on assumptions and the dynamic response. Such a system is described in U.S. Pat. No. 6,122,601. Unfortunately, this system is also strongly dependent on accurate assumption inputs to its algorithm(s). In addition, a base material exhibiting a certain dynamic vibrational response to a known input does necessarily mean that the base material can statically and rigidly support the weight of construction resting on the base material.

Apart from all of these compaction monitoring devices, there has been long reliance upon the skill and experience of compactor operators to determine when a supporting layer has been adequately compacted based upon qualitative feel and observations. Still, none of these strategies are useful in reducing downtime associated with waiting for a compaction quality assurance test to be performed and completed.

The present invention is directed to overcoming one or more of the disadvantages set forth above.

SUMMARY OF THE INVENTION

In one aspect, a method of compacting a base material includes a step of moving a compactor over the base material. Quality control compaction data for the base material is gathered at least in part by quantifying a sinkage deformation interaction between the compactor and the base material. Compaction quality assurance data is determined from the quality control compaction data.

In another aspect, a compactor includes a roller rotatably attached to a chassis. An electronic data processor is carried by the chassis, and includes a compaction quality control algorithm and a compaction quality assurance algorithm. The compaction quality control algorithm includes a means for quantifying a sinkage deformation interaction between the compactor and the base material. The compaction quality assurance algorithm uses data from the compaction quality control algorithm.

DETAILED DESCRIPTION

Figure 1:
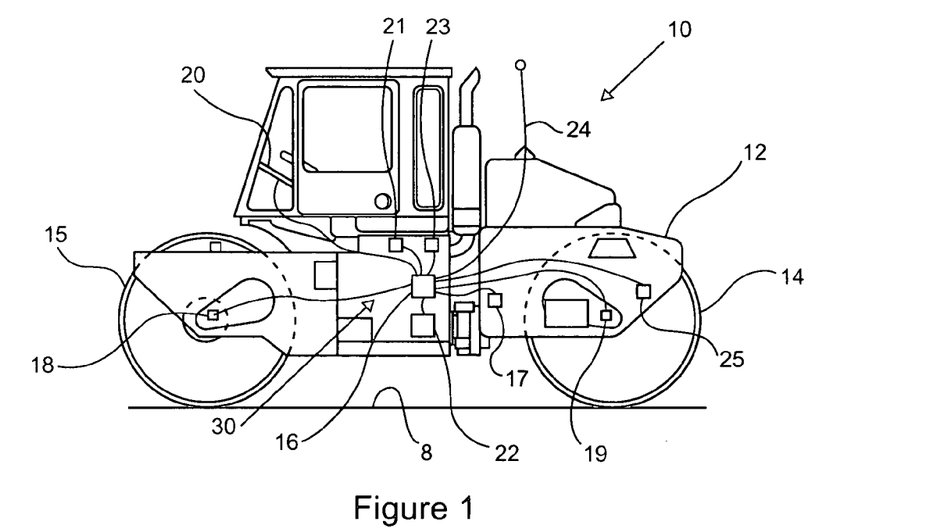
FIG. 1 is a side diagrammatic view of a compactor according to one aspect of the present invention.

Referring to FIG. 1, a compactor 10 includes a pair of rollers 14 and 15 that are rotatably attached to a chassis 12. Although compactor 10 is self propelled, the present invention finds potential application to towed compacting rollers as well. In addition, although rollers 14 and 15 are shown as smooth for an application such as asphalt, the present invention also finds potential application to tipped rollers used in applications such as compacting waste in a landfill or compacting soil for other earthworks construction. Compactor 10 includes an onboard computer 16 that can receive signals from various inputs including sensors 17–19, 21, 23, and 25 and a position data receiver 24. Computer 16 includes a compaction algorithm that processes the sensor data to determine a compaction state of the base material 8, preferably in real time as compactor 10 is moving over the base material. This compaction data can then be stored in data storage device 22 and/or displayed to an operator on display panel 20.

Those skilled in the art will appreciate that as compactor 10 moves over base material 8, there is a sinkage deformation interaction between the two. In other words, the base material will support the weight of the compactor, but the base material will deform (decrease in thickness) as the compactor moves over the base material. The sinkage deformation interaction will decrease with each successive pass over the base material until the same is fully compacted. The present invention recognizes that there is probably no better predictor of how well the base material can support, without substantial deformation, the weights of moving vehicles or static structures, than its ability to support a heavy compactor without substantial deformation. The present invention seeks to use information available to the compactor, such as via sensors, to quantify the compactor sinkage interaction with the base material to determine the compaction state of the same. This compaction data would normally be characterized as quality control compaction data for use by the operator in monitoring the compaction state of the base material during the compaction process. However, the present invention goes further by using the quality control compaction data to determine quality assurance compaction data for the base material. As confidence and reliability grow in the accuracy of the determined quality assurance compaction data, the need for post processing quality assurance testing can be reduced, if not eliminated. Thus, the present invention preferably generates real time quality control compaction data for use by an operator in determining when the compaction is complete, but goes further to use this data to generate quality assurance compaction data (e.g., results of a proof rolling test) so that the construction process can proceed without the delay and expense associated with post process quality assurance testing.

The present invention contemplates using at least one of three strategies for determining quality control compaction data relating to a sinkage interaction between the compactor and the base material. These strategies include an energy interaction between the compactor and the base material as taught in co-owned U.S. Pat. No. 6,188,942, determining compaction state by monitoring data indicative of an effective roller radius, or measuring a rut depth as discussed infra. The present invention also contemplates combining more than one compaction state determination technique in order to arrive symbiotically at an even more accurate determination of both quality control data and what a quality assurance compaction test would reveal. Thus, the present invention might combine two or more quality control compaction data sets, with at least one of the data sets reflecting compactor sinkage interaction data.

Those skilled in the art will appreciate that the energy transfer measurements taught in co-owned U.S. Pat. No. 6,188,942 can be characterized as compaction sinkage interaction data. This reference teaches that the compaction state can be determined either by determining a level of compactive energy delivered to the base material or by determining the compaction performance as a function of the propelling power consumed in moving the compactor over the base material. In either case, the ground speed of the compactor is determined in any of a number of known ways, such as by use of a ground speed sensor or by determining ground speed using position related data in a manner well known in the art. Another aspect common to both of the energy interaction techniques relates to determining a lift thickness of the base material, which can be accomplished in a number of ways known in the art, such as via a site coordinate determining system, by using laser plane systems, GPS systems, manual survey techniques, and the like. Those skilled in the art will recognize that the base material's lift thickness will decrease as the material is compacted. Another variable used in common by the energy interaction technique is to determine the width of the compaction roller, which can or should be a known quantity. The position determining system according to the aspect of the invention can be gained in a number of known ways such as via the GPS position receiver 24, by using lasers, dead reckoning, or some other type of system known in the art. Finally, the compactive energy interaction data requires a determination of rolling resistance encountered by the compactor 10 as it moves over base material 8. In the case of self propelled compactor 10, this information can be gained by using an input sensor 21 and an output sensor 23 that are operably coupled to sense conditions at the input and output of a torque converter (not shown), which is central to propelling the compactor over the base material. These sensors are preferably suited for sensing at least one of pressure, speed, and torque of the torque converter and can be used to determine a corresponding differential pressure, differential speed and/or differential torque at the torque converter as a means of determining the rolling resistance of the compactor with respect to the base material.

Preferably, the compactive energy can be determined by the equation.

Equation 1:
$$CE = \frac{R}{T * W}$$

Where CE is the compactive energy, R is the rolling resistance, T is the lift thickness and W is the compaction width. Those skilled in the art will appreciate that the compactive energy is a measurement of the sinkage interaction between the compactor and the base material. Thus the quality control compaction data is, or can be determined as a function of the compactive energy. In one alternative, the compactive energy delivered by compactor 10 to base material 8 is accumulated during successive passes. When the accumulated total compactive energy delivered reaches a desired predetermined value, the compaction is complete. For example, the predetermined value may be determined by testing and prior experience showing the total compactive energy needed to compact the base material is a certain desired amount. In an alternative, the compactive energy being delivered by the compactor to the material is monitored as the pass occurs. The amount of compactive energy delivered will decrease until an asymptotic value is reached, i.e., the amount of decrease in compactive energy delivered is below a threshold. Compaction is complete when the amount of compactive energy delivered on a pass is below a predetermined value. Alternatively, the compaction may be considered to be complete when the difference in compaction energy delivered from pass to pass is determined to be below a predetermined value.

Those skilled in the art will appreciate that propelling power corresponds to the compactive energy delivered by the compactor to the base material, and need not necessarily need a determination of base material lift thickness in order to calculate the compaction state. Preferably, the propelling power is determined as the product of ground speed and rolling resistance. However, alternative methods for determining the propelling power of the compactor may be used, such as the product of torque and rotational velocity, the product of hydraulic flow rate and hydraulic pressure, and rate of fuel consumption. In addition, the energy interaction strategy according to the present invention is preferably made more accurate by factoring in data such as an inclinometer sensor 17, internal energy loss rates of compactor 10 due to bearings, gears, hydraulic fluid and the like, the rate or gain of potential energy of the compactor, and the rate of wind energy being applied to the same. Taking into consideration these phenomena will increase the accuracy of any determination of quality control compaction data.

Apart from the energy interaction strategy for quantifying a sinkage deformation interaction between the compactor and the base material, the present invention also recognizes that the compaction state can be determined by monitoring the effective roller radius of the compactor as it moves over the base material. This aspect of the invention utilizes different sensors, namely sensors 18 and 19 for generating data indicative of an effective roller radius as a means of indicating compaction state. Depending upon the particular compactor and the chosen strategy, sensors 18 and 19 can take on a variety of forms. For instance, in one aspect, sensors 18 and 19 can be roller rotation sensors, which could sense roller angular position and/or rotation rate of the respective rollers 15 and 14. In another aspect, sensors 18 and 19 could be ground clearance sensors that measure the ground clearance level of chassis 12 above the adjacent base material 8.

Figure 2:
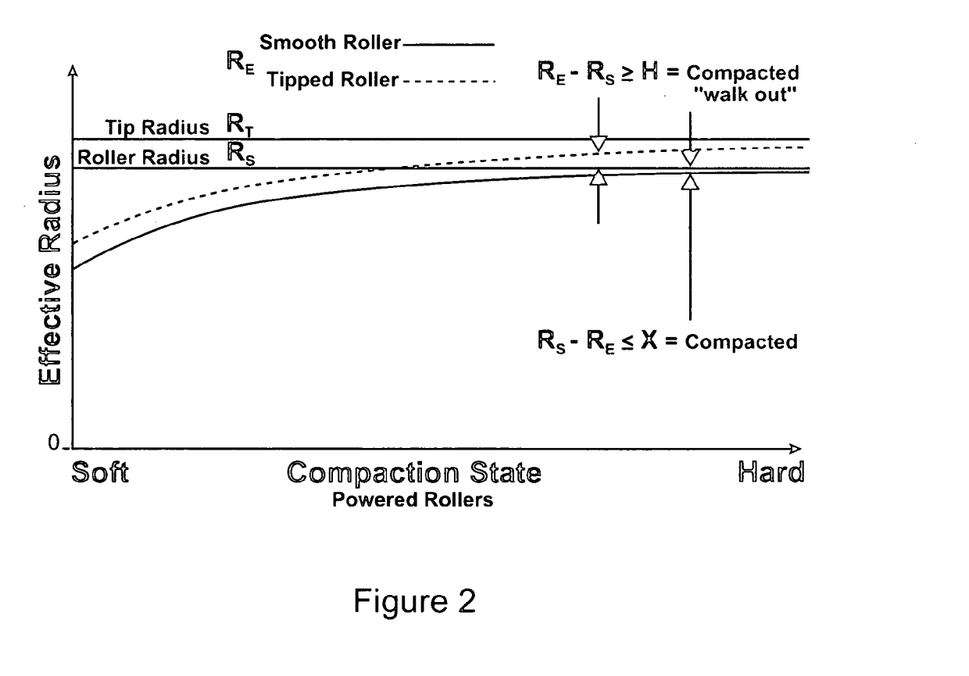
FIG. 2 is a graph of effective roller radius to compaction state for both tipped and smooth powered rollers according to the present invention.

Referring to FIG. 2, the present invention recognizes that the effective roller radius of a compactor will change as a base material is being compacted. Effective rolling radius $R_e$ is defined as the compactor travel distance per wheel revolution divided by two pi. When the compactor 10 of FIG. 1 begins a compacting job, it will start somewhere on the solid curved line. In other words, when the compacting job is initiated, the base material will be relatively soft and the effective radius of the roller will be substantially, and measurably, smaller than the actual roller radius $R_s$. As the material becomes harder with each pass of the compactor, one will move toward the right on the solid curved line. As the number of passes increases, the effective radius $R_e$ will asymptotically approach the actual radius $R_s$. When the difference X between the actual roller radius $R_s$ and the effective roller radius $R_e$ is less than some predetermined quantity, the base material can be said to be compacted. Those skilled in the art will recognize that the present invention insightfully recognizes that the compaction state of the underlying base material can be determined by measuring how well the base material supports the compactor. This in turn is determined by the effective rolling radius of the compactor as it moves over the base material.

Figure 3A:
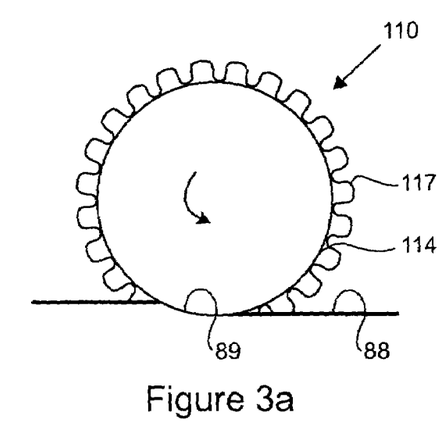
FIG. 3a and FIG. 3b are side views of a tipped roller when the base material is soft and hard, respectively.
Figure 3B:
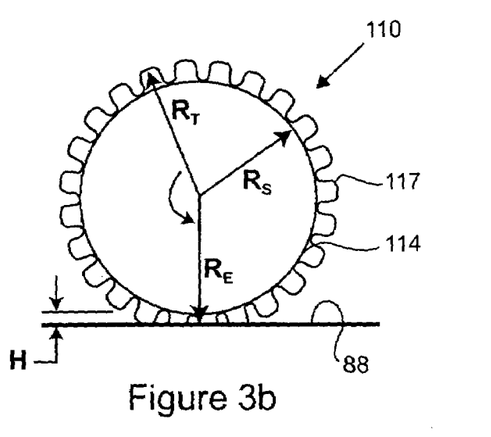

Referring now in addition to FIGS. 3a and 3b, the compactor 110 with a tipped roller 114 is shown moving over a base material 88 when soft and when hard, respectively. In particular, base material 88 could be waste in a landfill, and as compactor 110 moves forward, both the smooth portion of roller 114 and tips 117 compact the base material 88 in the region 89. The compaction state of base material 88 in FIG. 3a would be somewhere in the soft region of the dashed line of FIG. 2 representing effective radius of a tipped roller. After a number of passes over a base material 88, compactor 110 would arrive at the state shown in FIG. 3b where the smooth surface of roller 114 is actually lifted out of contact with base material 88 by the weight of the compactor being supported on tips 117. When the clearance distance between the smooth surface of the roller 114 and the base material 88 is greater than a distance H, the waste or soil can be said to be compacted. Those skilled in the art will recognize that FIG. 3b is associated with a commonly observed phenomenon known as "walk out". "Walk out" is the response of the compaction machine as ground density and firmness increases. It is the decrease in roller sinkage and compactor tip penetration that occurs as ground strength increases in the compaction process. "Walk out" is commonly used in the field and is typically based solely on visual information by sight managers and inspectors. The present invention preferably quantifies the compaction state by quantifying the distance H achieved when the compactor is in a so called "walk out" state.

Although the present invention is preferably implemented by actually determining the effective roller radius of the compactor at various locations on the base material, those skilled in the art will appreciate that the present invention can be practiced by utilizing a variable indicative of, but not necessarily the same as, effective roller radius. For instance, one such alternative measure would be to utilize ground clearance sensors to periodically measure the distance between the sensor (chassis location) and the surface of the adjacent base material not compacted in the current pass. Although the present invention encompasses such an alternative, it is not preferred for a number of reasons. Among these reasons would be that measuring ground clearance could be problematic and could require costly transducers, which themselves could be subject to damage or could lack robustness for adverse conditions of dust and mud. In addition, the base material is rarely smooth and is most often irregular, thus requiring a topography or smoothing algorithm to determine what the average level of an irregular base material surface is. Nevertheless, those skilled in the art will appreciate that a wide variety of choices could be made with regard to ground clearance sensors including contact or non-contact devices. The ground clearance sensors could include but are not limited to sonic, infrared, radar and even gage wheels.

In a more preferred alternative, a likely more robust method would not require ground interacting transducers. In this alternative method, the relative wheel rolling radius can be determined from known compactor ground speed and a determined roller rotation speed. The availability of ground position through technology such as the global positioning system (GPS) makes the measure of true ground speed very accurate and available. Nevertheless, there are also alternatives to position information to measure true ground speed such as radar devices or even using a gage wheel. Wheel speed can easily be measured with any of the known transducers often used for rotational drive line or wheel hub speed sensing. Combining these two measures and comparing the difference between the two will reveal the compaction state of the base material. Recalling, effective rolling radius is defined as the machine travel distance per wheel revolution divided by two pi. Thus, in this embodiment of the present invention, the quality control compaction data includes data that is, or is indicative of, the effective roller radius of the compactor at different locations on the base material.

Figure 4:
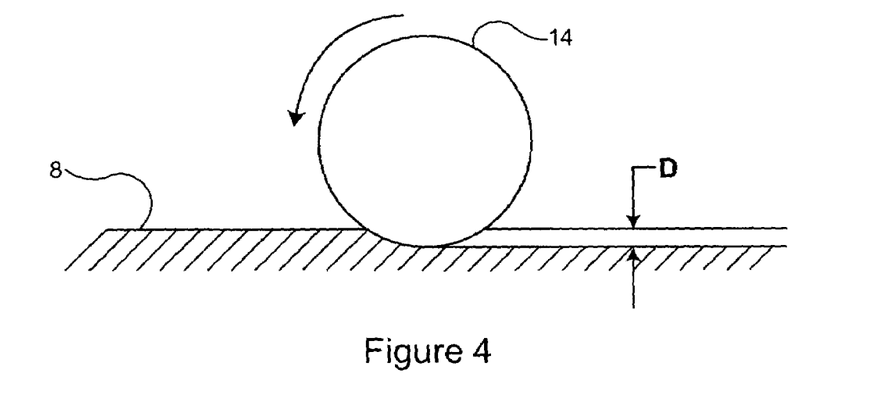
FIG. 4 is a side schematic view of the compactor of FIG. 1 moving over a base material according to another aspect of the present invention.

Referring to FIG. 4, still another strategy for determining a sinkage deformation interaction between a compactor and a base material is shown schematically via roller 14 moving over base material 8. As the compactor moves over the base material it will produce a rut relative to the adjacent base material. Thus, in this aspect of the invention, some means carried by the compactor is used to measure a rut depth D, and the same is used as quality control compaction data. Those skilled in the art will appreciate that rut depth D can be measured in a number of ways using contact or non-contact sensors. Although this strategy is contemplated in relation to the present invention it is less preferred currently the availability of rut depth measuring devices that can both produce accurate results and withstand the hostile environment surrounding the compactor are extremely expensive in the least, and do not exist in the opinion of some. In addition, continuously measure rut depth may find better applicability in some compacting applications than others. For instance, continuously measuring rut depth with compacting waste in a landfill may not be entirely realistic, but continuously measuring rut depth when compacting pavement or a similar base material could be much more realistic, due at least in part to the more homogenous nature of the material being compacted.

Figure 5:
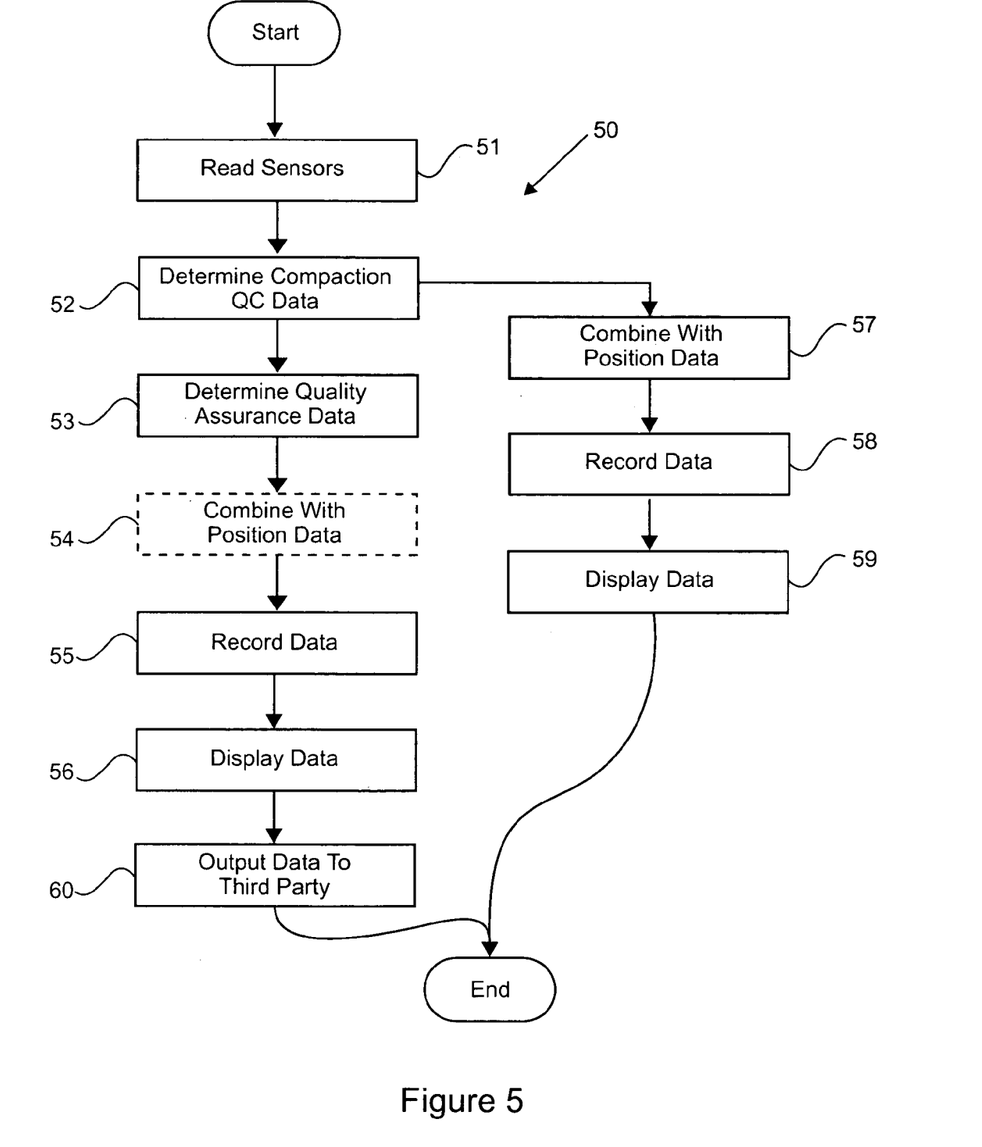
FIG. 5 is a flow diagram of a compaction algorithm according to the present invention.

Referring to FIG. 5, an example compaction algorithm 50 is illustrated in the manner of a flow diagram. Those skilled in the art will appreciate that computer 16 of FIG. 1 would be programmed to include compaction algorithm 50. Compaction algorithm 50 initially includes a step of reading the sensor inputs 51. Next, the sensor input data is used by a compaction quality control algorithm 52 to determine quality control compaction data that represents the compaction state of the base material. In a preferred embodiment, this is done using an effective roller radius determiner that utilizes the insight from the graph of FIG. 2 to determine the compaction state, preferably in real time, by a comparison of the actual roller radius to the effective roller radius. In the case of a tipped roller, such as that used for soil or waste compaction, the compaction state determination algorithm 52 might also include a walk out determiner, and/or a ground clearance determiner. For instance, if the sensor is used for a ground clearance determination, one could expect the compaction algorithm 50 to utilize the ground clearance determiner. However, in most instances the invention will use the effective roller radius determiner as the primary portion of its compaction state determination algorithm 52. Nevertheless, the quality control compaction data could be based upon an energy interaction between the compactor and the base material as discussed above, and/or a rut depth determiner as a substitute way of measuring a sinkage deformation interaction between the compactor and the base material. After the compaction state has been determined, the compaction state data is linked to position data at 57 so the compaction state of the entire surface can be mapped. Next, the data is recorded at step 58 and finally displayed in step 59. Those skilled in the art will appreciate that the display can take on a variety of forms, but is preferably graphical in nature, which may include colors or gray scales to indicate the level of compaction in each unit area of the base material. Thus, the operator could view their display and quickly determine where and how to operate the compactor to most efficiently compact the base material and to ascertain when the base material is completely compacted.

In addition to gathering quality control compaction data, the present invention also determines quality assurance compaction data. Although FIG. 5 shows this determination being performed in parallel with the processing of the quality control compaction data, it could be done subsequent to completion of a compaction process or possibly require a control command from an operator or another person to perform the determination of quality assurance compaction data as per box 53. This is done using a compaction quality assurance algorithm that transforms, if needed, the compaction quality control data into compaction quality assurance data using correlations and/or functional relationships gained through testing, observation, calculations and the like. As stated earlier, quality assurance compaction data can take on a number of forms depending upon the nature of the base material, the nature of the construction project, the jurisdiction in which the compaction is occurring, among other factors known in the art. For instance, for road construction in one jurisdiction, a proof rolling test might be quality assurance test required for verification that the base material is adequately compacted. In another jurisdiction for the compaction of waste material in a landfill, the quality assurance test might consist in determining whether the compactor will "walk out" on the supposedly compacted waste. In still another jurisdiction, a pavement surface may be considered properly compacted when either a destructive or non-destructive density test shows a density above some pre-determined threshold. In all versions of the present invention, the compaction quality assurance data is based upon the compactor sinkage interaction data generated for quality control purposes. Although the quality control compaction data is quantitative, the quality assurance data need not necessarily be. In other words, the quality assurance data could be as simple as a yes or a no as to whether the base material would pass a quality assurance test. Nevertheless, the quality assurance data could also be quantitative as to a single number as to what a quality assurance test would reveal (e.g., proof rolling rut depth, troxler density test result, etc.). Although in most instances the quality assurance data would be simpler in form and smaller in content that the quality control compaction data, it can take on the same richness and complexity as the quality control compaction data. For instance, the quality assurance data could be quantified for the particular post processing test and could be mapped against locations by combining the same with position data as in box 54. The quality assurance data is preferably recorded as per box 55 and displayed if desired, either at the operator control station or elsewhere, such as via telemetry. Finally, the quality assurance data can be outputted in a suitable format, such as electronically or in a document format, to a third party inspector. This could enable the compaction process to be documented and potentially provide a written assurance that the base material is adequately compacted so that the construction project can proceed in haste without the cost and expense associated with waiting for a post processing test to be performed.

Those skilled in the art will appreciate that the quality control compaction data could be converted into quality assurance compaction data using empirical data, testing, equations or any other suitable manner known in the art that will provide the requisite accuracy. The present invention recognizes that compactor sinkage interaction data will always be related either causationally or via a correlation to virtually any quality assurance requirements currently known for testing the compaction state of base materials.

INDUSTRIAL APPLICABILITY

The present invention finds potential application in any compactor that includes a roller. Although the present invention has been illustrated in the context of powered smooth or tipped rollers, the present invention also finds potential application in the case of towed rollers. However, those skilled in the art will appreciate in the case of towed rollers, the effective radius of the roller will start out greater than its actual radius and will asymptotically approach from above the actual radius as the base material is compacted. This is the opposite of the powered rollers illustrated in FIG. 2 that asymptotically approach the actual radius from below. Nevertheless, those skilled in the art will appreciate that the same principals used with regard to powered rollers to determine compaction state based upon data indicative of effective roller radius could also apply to towed rollers as well.

Those skilled in the art will appreciate that the effective roller radius of the compactor can be monitored in a number of ways. For instance, one could calculate a ratio of the actual ground speed to the rotation rate of the roller without ever actual calculating the effective roller radius. In addition, one could also monitor effective rolling radius by determining the ratio of ground distance traveled to the number of rotations undergone by the roller to traverse that distance. Thus, those skilled in the art will appreciate that the invention can be practiced by merely sensing data indicative of an effective roller radius rather than actually calculating effective roller radius in order to ascertain the compaction state of the base material.

The present invention advantageously provides a means for determining and displaying compaction state data in real time during a compacting operation. This information can be used by the operator to more efficiently maneuver the compactor over the base material to hasten the rate at which the entire surface is compacted. In addition, the present invention should allow for quality control compaction data over an entire surface that will allow for a reduction in a need for costly rework and adjustment to specifications due to a failure to meet compacting specifications at one or more locations on the base material. The present invention recognizes that there may be no better determination of compaction status than the ability of the base material to support the compactor with deflection less than some predetermined value. In the case of a smooth roller, this value X relates to a maximum acceptable difference between the actual radius and the effective radius of the compactor when the material is hard and suitably compacted. In another aspect for tipped rollers, walk out has occurred, and hence the ground is compacted, when the difference between the effective radius and the smooth surface of the roller is greater than or equal to some walk out height H.

Those skilled in the art will recognize that the present invention measures a machine response regarding sinkage deformation as a direct quantification of compaction state to quantify the level and value of compaction both to qualify the base material prior to adding surface materials such as the base under a pavement layer, and also to quantify the level and value of compaction to qualify the final compaction result. In addition, the present invention preferably uses the measured machine values as the quality assurance data, replacing the current practice of using measured earth material density or measured sinkage and rutting from a truck proof rolling as the quality assurance values.

The present invention also recognizes that their can be a symbiotic relationship between separate and different means of determining the compaction state of a base material. For instance, a preferred version of the present invention would utilize both an energy transfer algorithm for determining compaction state as well as an effective rolling radius algorithm strategy. These two different compaction data determination could then be merged by a data merging algorithm to arrive at merged data that would likely be more accurate than compaction data garnered from a single set of sensors with a single strategy. The present invention also contemplates combining deflection sinkage interaction data with other types of data including but not limited to vibration response data, and various means of estimating base material density.

There are at least two primary benefits from the present invention. First, the need for secondary measurements of compaction are eliminated and thus both time and cost of earth works construction is reduced. One of the major time factors is not the actual measurement time, but the wait time between completion of a compaction process and the quality assurance measurement function. The density measurement of compaction is typically performed using a nuclear density gage by a geotechnician. The nuclear density device requires a license to own and a certified operator, and the technician performing the measurements is typically an employee of a construction engineering firm, not an employee of the construction contractor performing the compaction. This relationship often leads to time delays between when the compaction operator has completed the process until the geotechinician completes the measurement process. Then, if there is a failure to meet specifications, further delays can occur to determine what, and how extensive a re-work, will be required to correct for failures. The direct measure of a compactor sinkage interaction to determine compaction state, and then using that quality control data to determine an expected proof rolling test result as the compaction criteria both eliminates the delay waiting for the measurement process, and can prevent failures by identifying success as part of the process control.

The second primary benefit is the more direct measure of compaction quality utilizing the proof rolling type information. As previously noted, density is a very indirect measure of compaction quality since it is not a direct measure of the compaction requirement. Proof rolling is a much more direct measure of the compaction requirement, particularly for structure such as road beds, pavement surfaces, and foundations where the requirement is to support heavy loads. The current practice of using density measurement to validate the quality of an earthen structure is subject to significant error due to variability of construction materials, moisture content and density measurement errors, among other reasons. Using the ability of the earthen structure to support the load of the compaction machines with less than some threshold deformation is a much more direct and less error prone measurement of compaction quality. In other words, the ability to measure the sinkage deformation interaction between the compactor and the base material provides a direct indication of the ability of the earthen structure to support heavy loads. This more direct measure will lead to higher quality earthen structures with less probability of failure thereby reducing costs associated with failure and repair.

A third benefit closely related to the second benefit could be defined as the 100% quality assurance that can be attained with compaction machine measurements. It is usually only the compaction machine that has been in contact with the entire surface of an area to compacted. The density measurements commonly used today are spot checks where the actual volume of material measured is over a same area, no more than a six inch radius, and to a small depth, typically only two to four inches. It is also common to take only one measurement for hundreds up to even thousands of yards of material. Therefore, only a very small fraction of the earthen structure is actually validated to meet compaction requirements. The present invention, however, allows for quality assurance data covering 100% of every unit volume of material compacted during the process. In fact, the present invention allows for compaction quality assurance to evolve from a post processing spot check to quantified quality assurance data covering an entire area being compacted. For instance, while the quality control compaction data may be based upon an effective roller radius, this data can then be transformed into an equivalent quality assurance data set that quantifies what a proof rolling test result would be for each unit area of the entire surface of the base material.

Those skilled in the art will recognize that compaction quality assurance data according to the present invention includes but is not limited to a proof rolling test result, a walk out test result, a penetrometer test result, a base material density test result, and possibly even compactor sinkage into the base material. Depending upon the specifications for the particular compacting job, at least one of these quality assurance tests is required in order to continue with post compaction construction. The expected quality assurance test results are based upon the quality control compaction data that includes a quantification of a sinkage deformation interaction between the base material and the compactor. This interaction includes data garnered from on board sensors that are indicative of at least one of an energy interaction between the compactor and the base material. An effective data indicative of an effective roller radius of the compactor, and direct measurement of a rut depth produced by the compactor as it moves over the base material. The present invention also recognizes that compaction quality assurance may evolve in the future to a quantification of compactor sinkage deformation into the base material. Again, the present invention recognizes that there is probably no better indication of compaction state than the ability of the base material to support a heavy compactor while undergoing deformation that is less than some threshold amount. As the industry comes to recognize this, the present invention contemplates that compaction quality assurance requirements may be base upon a quantification of compactor sinkage deformation into the base material, which is related, or possibly even identical to, compactor quality control data based upon a sinkage deformation interaction between the compactor and the base material.

It should be understood that the above description is intended for illustrative purposes only, and is not intended to limit the scope of the present invention in any way. Thus, those skilled in the art will appreciate that other aspects, objects, and advantages of the invention can be obtained from a study of the drawings, the disclosure and the appended claims.

What is claimed is:

1. A method of compacting a base material, comprising the steps of:
    moving a compactor over the base material;
    gathering quality control compaction data for the base material at least in part by quantifying a sinkage deformation interaction, which is other than a density of the base material, between the base material and the compactor; and
    determining compaction quality assurance data from the quality control compaction data.

2. The method of claim 1 wherein the quantifying step includes at least one of:
- determining data indicative of an effective roller radius of the compactor;
- measuring an energy interaction between the compactor and the base material; and
- measuring a rut depth in the base material caused by the compactor.

3. The method of claim 2 wherein the gathering step includes first quality control compaction data at least in part by reading a first set of sensors; and
the method including the step of gathering second compaction quality control data at least in part by reading a second set of sensors.

4. The method of claim 3 including a step of merging the first compaction quality control data and the second compaction quality control data.

5. The method of claim 1 including a step of providing the compaction quality assurance data to a third party inspector.

6. The method of claim 1 wherein the compaction quality assurance data includes data indicative of at least one of;
- a proof rolling test result;
- a walk out test result;
- a penetrometer test result;
- a base material density test result; and
- compactor sinkage into the base material.

7. The method of claim 1 wherein the determining step includes a step of determining the compaction quality assurance data for a predetermined area of the base material.

8. The method of claim 1 including a step of linking at least one of the quality control compaction data and the quality assurance compaction data to compactor position data.

9. The method of claim 1 wherein the determining step is performed in real tine with the moving step.

10. The method of claim 1 including a step of displaying at least one of the compaction quality control data and compaction quality assurance data during the moving step.

11. A compactor comprising:
- a chassis;
- a roller rotatably attached to said chassis;
- a computer carried by said chassis, and including a compaction quality control algorithm and a compaction quality assurance algorithm;
- said compaction quality control algorithm including means for quantifying a sinkage deformation interaction, which is other than a density of the base material, between the base material and the compactor; and
said compaction quality assurance algorithm using data from said compaction quality control algorithm.

12. The compactor of claim 11 wherein at least one of said compaction quality control algorithm and said compaction quality assurance algorithm includes a compactor sinkage determination algorithm.

13. The compactor of claim 11 wherein said interaction includes at least one of:
- an effective roller radius of said compactor,
- an energy interaction between said compactor and the base material, and
- a rut depth in the base material caused by said compactor.

14. The compactor of claim 13 including a first set of sensors carried by said chassis and being associated with a first compaction quality control algorithm; and
a second set of sensors carried by said chassis and being associated with a second compaction quality control algorithm included with said computer.

15. The compactor of claim 14 wherein said computer includes a compaction data merging algorithm that uses data from said first compaction quality control algorithm and said second compaction quality control algorithm.

16. The compactor of claim 11 including means for delivering compaction quality assurance data produced by said compaction quality assurance algorithm to a third party inspector.

17. The compactor of claim 11 wherein said compaction quality assurance algorithm produces data indicative of at least one of:
- a proof rolling test result;
- a walk out test result;
- a penetrometer test result;
- a base material density test result; and
- compactor sinkage into the base material.

18. The compactor of claim 17 wherein said data encompasses a predetermined area of said base material.

19. The compactor of claim 11 wherein at least one of said compaction quality control algorithm and said compaction quality assurance algorithm is linked to a compactor position determination algorithm.

20. The compactor of claim 11 including a real time display of at least one of compaction quality control data and compaction quality assurance data.

* * * * *